US009519158B2

(12) United States Patent
Brudz

(10) Patent No.: US 9,519,158 B2
(45) Date of Patent: Dec. 13, 2016

(54) TACTICAL LIGHTING UNIT WITH SYNCHRONIZED EYE PROTECTION

(71) Applicant: John Jason Brudz, Bolton, CT (US)

(72) Inventor: John Jason Brudz, Bolton, CT (US)

( * ) Notice: Subject to any disclaimer, the term of this patent is extended or adjusted under 35 U.S.C. 154(b) by 149 days.

(21) Appl. No.: 14/510,514

(22) Filed: Oct. 9, 2014

(65) Prior Publication Data

US 2016/0062148 A1   Mar. 3, 2016

Related U.S. Application Data

(60) Provisional application No. 61/889,249, filed on Oct. 10, 2013.

(51) Int. Cl.
| | | |
|---|---|---|
| *G02F 1/1335* | (2006.01) | |
| *G03B 15/02* | (2006.01) | |
| *G02C 7/10* | (2006.01) | |
| *G02F 1/133* | (2006.01) | |
| *F41H 13/00* | (2006.01) | |
| *A61F 9/02* | (2006.01) | |

(52) U.S. Cl.
CPC .......... *G02C 7/101* (2013.01); *F41H 13/0056* (2013.01); *G02C 7/104* (2013.01); *G02F 1/13306* (2013.01); *A61F 9/023* (2013.01)

(58) Field of Classification Search
CPC ........ F21K 5/02; F21K 5/023; G03B 15/0442; G03B 15/0457; G03B 15/05; G02F 1/13471; G02C 7/101; A61F 9/067; A61F 9/023; B23K 9/32

USPC .............................................. 362/10; 349/14
See application file for complete search history.

(56) References Cited

U.S. PATENT DOCUMENTS

| | | | |
|---|---|---|---|
| 5,685,636 A | 11/1997 | German | 362/259 |
| 6,070,264 A | 6/2000 | Hamilton et al. | 2/8 |
| 6,283,609 B1 | 9/2001 | Parsons et al. | 362/187 |
| 6,841,772 B1* | 1/2005 | Hamilton | A61F 9/065 250/201.1 |
| 7,828,434 B2* | 11/2010 | Coulter | G02C 7/16 351/159.45 |

OTHER PUBLICATIONS

Tucker, Patrick, "The Military Is About to Get New Spy Glasses", Defense One, http://www.defenseone.com/technology/2014/06/military-about-get-new-spy-glasses/87292/, Jun. 25, 2014, 5 pages.

* cited by examiner

*Primary Examiner* — Mike Qi
(74) *Attorney, Agent, or Firm* — Harrington & Smith

(57) ABSTRACT

In accordance with an example embodiment of the present invention, an apparatus is disclosed. The apparatus includes a control unit, a light source, and an eye protection device. The light source includes a first timing circuit. The light source is configured to emit light. The first timing circuit is configured to control a flashing of the light emitted by the light source. The eye protection device includes a second timing circuit and a lens portion. The second timing circuit is configured to adjust a transparency and an opacity of the lens portion. The control unit is configured to synchronize the flashing of the light emitted by the light source with the opacity of the lens portion.

20 Claims, 5 Drawing Sheets

TACTICAL LIGHTING UNIT WITH SYNCHRONIZED EYE PROTECTION

CROSS REFERENCE TO RELATED APPLICATION

This application claims priority under 35 U.S.C. §119(e) to U.S. provisional patent application No. 61/889,249 filed Oct. 10, 2013 which is hereby incorporated by reference in its entirety.

BACKGROUND

1. Field of the Invention

The invention relates to a system providing a tactical lighting unit and synchronized eye protection.

2. Brief Description of Prior Developments

Technological improvements in law enforcement and military applications are ever evolving. One area that has gained popularity in recent years is the use of non-lethal control devices. For example, tactical lights have served a role as a method of non-lethal force, used to temporarily blind and disorient targets.

However, despite the above advances, there is still a strong need in the art for improved devices that help minimize the use of force, reduce injuries, as well as minimize excessive force complaints. The present invention accomplishes the above needs in the art and also provides other advantages, as will be described in detail below.

SUMMARY

In accordance with one aspect of the invention, an apparatus is disclosed. The apparatus includes a control unit, a light source, and an eye protection device. The light source includes a first timing circuit. The light source is configured to emit light. The first timing circuit is configured to control a flashing of the light emitted by the light source. The eye protection device includes a second timing circuit and a lens portion. The second timing circuit is configured to adjust a transparency and an opacity of the lens portion. The control unit is configured to synchronize the flashing of the light emitted by the light source with the opacity of the lens portion.

In accordance with another aspect of the invention, a method is disclosed. Light is emitted from a light source. The emitted light includes a flashing light. A lens portion of an eye protection device is adjusted from a substantially transparent state to a substantially opaque state. The emitting of the light is synchronized with the adjusting of the lens portion.

In accordance with another aspect of the invention, a non-transitory computer readable medium embodied with a computer program is disclosed. The non-transitory computer readable medium embodied with a computer program includes computer program instructions which when loaded into a processor enable the processor to control a flashing light emitted from a light source. Adjust a lens portion of an eye protection device in response to the flashing light such that the lens portion is adjusted between substantially transparent and substantially opaque.

BRIEF DESCRIPTION OF THE DRAWINGS

The foregoing aspects and other features of the invention are explained in the following description, taken in connection with the accompanying drawings, wherein.

DETAILED DESCRIPTION

Figure 1:
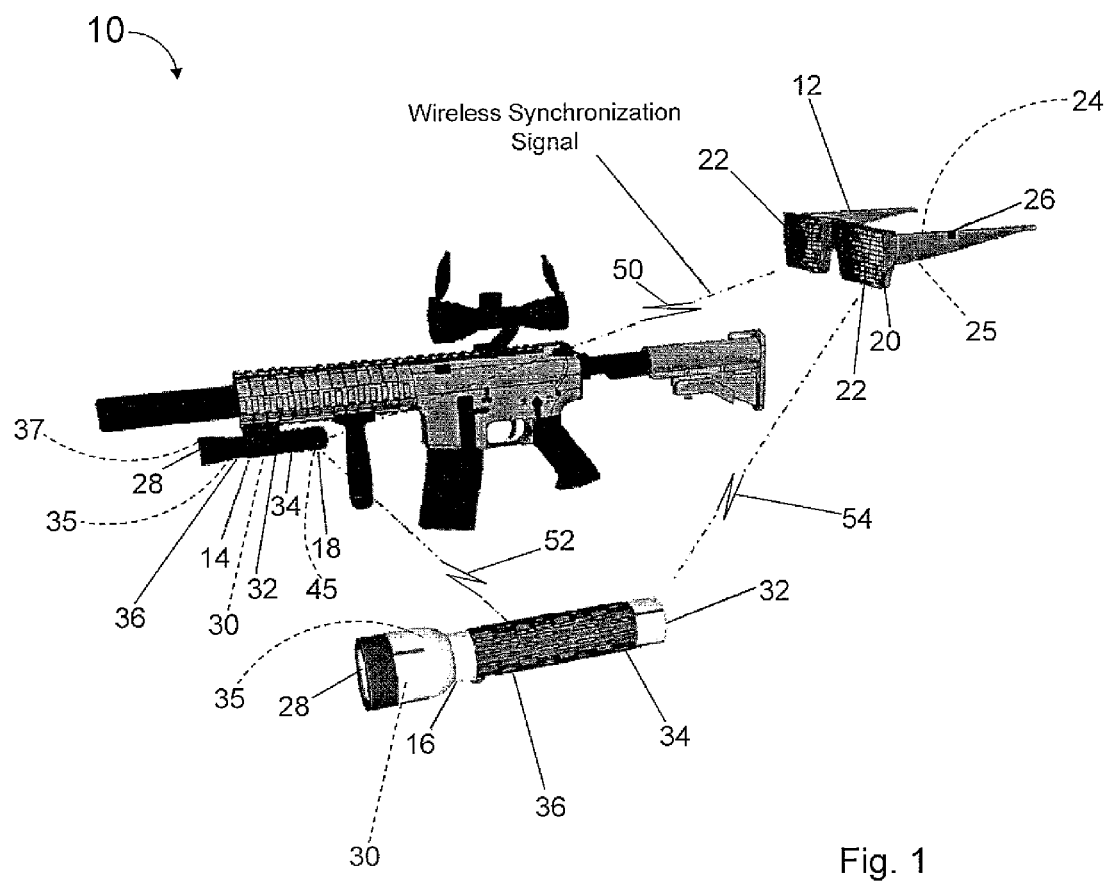
FIG. 1 is a perspective view of an environment control system incorporating features of the invention.

Referring to FIG. 1, there is shown a perspective view of an environment control system 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

The environment control system 10 is generally configured to provide synchronized eye protection corresponding to a tactical lighting unit. The system 10 provides for synchronized strobe lights to create a visually disruptive environment for all personnel within line-of-sight who are not equipped with properly synchronized compatible eye protection.

According to one example of the invention, the system 10 comprises one or more pairs of shutterglasses (or eye protection) 12, one or more light emitting units (or light sources) 14, 16, and a control unit (CU) 18. It should be noted that in alternate embodiments, the system 10 can have any other suitable type of features.

The shutterglasses 12 are suitably sized and shaped to be worn by a user. According to some embodiments of the invention, the shutterglasses 12 comprise liquid crystal display (LCD) shutterglasses. The LCD shutterglasses include a general size and shape of eyeglasses having a frame section 20 fitted with transparent liquid crystal display lenses 22. The lenses of the LCD shutterglasses 12 turn substantially visually opaque when a voltage is applied to them. The LCD shutterglasses 12 comprise some similar features as conventional shutterglasses which are used in applications, such as, 3D television, sports training and welding eye protection, for example. However, the LCD shutterglasses 12 comprise a highly accurate timing circuit 24 which controls the timing of the opacity of the glasses 12, and a wireless interface 25. For example, when the shutterglasses are properly synchronized with the light emitting units (LEUs) 14, 16, the glasses 12 turn opaque at precisely the same instant as the LEUs 14, 16 is emitting a very bright light, so that the wearer of the glasses 12 is protected from effects of the bright light. According to some embodiments of the invention, the shutterglasses may be configured for variable opacity duration. Additionally, the shutterglasses 12 may further comprise a synchronize button 26. However, it should be noted that a button is not required, and any suitable type of user input device may be provided, such as a switch, or a touch panel/screen/sensor, for example.

It should be understood that while various exemplary embodiments of the invention have been described in connection with LCD shutterglasses, one skilled in the art will appreciate that the invention is not necessarily so limited and that alternate embodiments may comprise any suitable type eye protection configured to be synchronized with the light emitting unit(s). For example, in some other embodiments, the eye protection 12 may comprise any suitable type of wearable device worn by a user proximate the head/face area, such as night vision devices (to prevent "flaring", for example), a head mounted display, smart glasses/goggles (such as Google Glass®, for example), wearable action cameras, near-eye displays, augmented reality glasses, virtual reality eyewear, or any suitable type of wearable technology with an optical head-mounted display (OHMD), for example. Additionally, the shutterglasses or eye protection may include ballistic protection, or the shutterglasses or eye protection may be configured to be worn over/under ballistic protection. Furthermore, in some embodiments, the shutterglasses may include conventional commercially available shutterglasses which are re-operated or modified to include features of the invention (such as the timing circuit, for example).

As shown in FIG. 1, the Light Emitting Units may be suitably sized and shaped as a tactical flashlight, or any other suitable weapon mounted light or a handheld flashlight, for example. The Light Emitting Units 14, 16, each comprise a light emitting portion 28, a timing circuit 30, a synchronizing button 32, and a wireless interface 35. According to various exemplary embodiments, the light emitting portion may comprise an incandescent bulb or light emitting diode mounted proximate a reflector (as in a flashlight, for example), a strobe light, or any other suitable light source. The timing circuit is similar to the timing circuit of the shutterglasses, such that the LEU is configured to fire the strobe (or emit light from the light emitting portion) only when synchronized with the LCD Shutterglasses. Additionally, in some embodiments the LEU can be provisioned with a digital ID number, so that each LEU in a multiple LEU environment can be individually assigned and controlled. In some exemplary embodiments, each LEU may be further equipped with an on/standby/off switch 34, and a mode selector 36.

According to various exemplary embodiments, the light emitting portion may be configured as a variable speed, high intensity, strobe unit providing about 0.5 to flashes per second (fps). Additionally, in some embodiments, the light emitting portion may be configured for variable flash duration.

Figure 2:
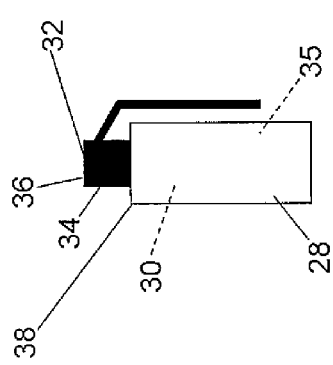
FIG. 2 is a front view of a another example of a light emitting unit incorporating features of the invention.

In the embodiment shown in FIG. 1, the LEU 14 is a weapon mounted LEU, and the LEU 16 is a hand-held LEU. However, it should be understood that any other suitable type of lighting unit(s) could be provided. Referring now also to FIG. 2, another embodiment of a light emitting unit is shown. In this embodiment the light emitting unit 38 comprises a light emitting portion 28, a timing circuit 30, a synchronizing button 32, and a wireless interface 35, substantially the same as the light emitting units 14, 16 shown in FIG. 1. Also similarly, the LEU 38 may be further equipped with an on/standby/off switch 34, and a mode selector 36. However, in this embodiment the light emitting unit is provided as a flash bang grenade. The flash bang grenade is configured to be synchronized similarly as the light emitting units 14, 16, to ensure that the flash occurs during a window when the shutterglasses are opaque. Additionally, in some other embodiments of the invention, the light emitting unit may comprise any other light generating devices, such as crew served lighting units mountable on vehicles, or synchronization with vehicle strobes for police operations.

It should further be understood that while various exemplary embodiments of the invention have been describe in connection with multiple light emitting units, some embodiments may be provided with only a single light emitting unit.

The Control Unit (CU) 18 is configured to manage the synchronization of the LEU's and LCD shutterglasses, and can provide for more complicated modes of operation such as occulting, patterned or sequential LEU activation. According to some exemplary embodiments of the invention, the control unit may also comprise a wireless interface 45.

The shutterglasses 12, the LEU's 14, 16 and the control unit 18 are equipped to be synchronized wirelessly via the wireless interfaces 25, 35, 45. In some embodiments of the invention, once synchronized, connection to the control unit may no longer be required. The highly accurate clock (or timing circuit) 24, 30 within each device (shutter glasses or light emitting unit) ensures that each unit will only flash during a given "window", during which time the shutter glass units will render the lenses 22 opaque.

According to some embodiments of the invention, weapon mounted LEUs, such as LEU 14 shown in FIG. 1, may further comprise a sensor 37, which can be mounted on the gun barrel or proximate the gun barrel, to provide for muzzle flash suppression. According to this embodiment, the sensor 37 is configured to trigger the shutterglasses to opaque (when a discharge of the weapon is sensed) so that the user of the weapon does not lose his/her own night vision when firing the weapon.

Figure 3:
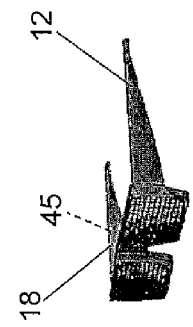
FIG. 3 is a perspective view of a another example of eye protection incorporating features of the invention.
Figure 5:
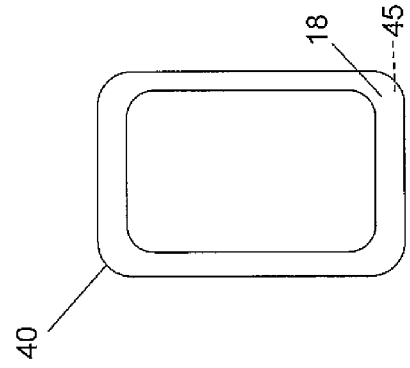
FIG. 5 is a front view of an electronic device incorporating features of the invention.
Figure 4:
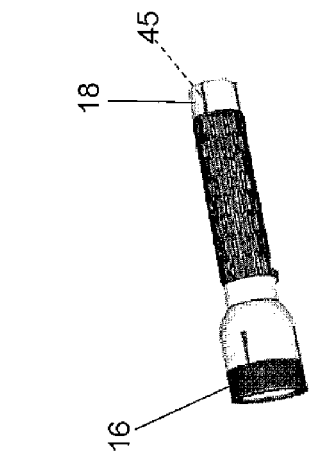
FIG. 4 is a perspective view of a another example of a light emitting unit incorporating features of the invention.

In the embodiment shown in FIG. 1, the control unit 18 is integral with the LEU 14. However, in alternate embodiments, any suitable location for the control unit may be provided. For example, in FIG. 3 there is shown an exemplary embodiment wherein the control unit 18 is integral with the shutter glasses 12. In FIG. 4 there is shown an exemplary embodiment wherein the control unit 18 is integral with the LEU 16. In some other embodiments of the invention, the control unit may be a stand alone device or may be part of an electronic device. For example, referring now also to FIG. 5, there is shown a multi-function portable electronic device 40 comprising the control unit 18. According to various embodiments, the electronic device 40 may comprise any suitable type of portable electronic device such as a mobile phone, a gaming device, a music player, a notebook computer, a tablet device, a wearable device, or a personal digital assistant, for example.

Additionally, it should be understood that in some embodiments of the invention, the controller unit can be integral with any combination of the LCD shutterglasses, the LEU's, or electronic device. Furthermore, in some embodiments of the invention the control unit may be directly connected with the corresponding integral component. For example, in the embodiment shown in FIG. 1, the control unit 18 may be directly connected to the LEU 14 and wirelessly connected to the shutterglasses 12 and the LEU 16. However, any suitable configuration may be provided.

In some other embodiments of the invention, the control unit may be provided as retrofit kit for existing tactical flashlights/strobes. For example, in some embodiments, a battery compartment cover may be replaced with a control unit enabled module.

It should be noted that the wireless interfaces 25, 35, 45 described above may comprise any suitable type of wireless communication, such as Bluetooth®, near field communication, or other similar secure short range digital radio technology.

For example, in some embodiments the wireless interface may be connected to a transmitter, a receiver, and an antenna 18 of the corresponding LEU, shutterglasses, or control unit, such that the wireless interfaces 25, 35, 45, provide for wireless communications with each other over the wireless links 50, 52, 54. In some other embodiments of the invention, the LEU, shutterglasses, and/or control unit may be connected via a digital interface such as micro USB, for example.

Additionally, in some other exemplary embodiments, the wireless interface and wireless links may be used in connection with existing cellular, GPS [global positioning system], or any other suitable antennas of the device.

According to one example of the invention, an exemplary usage or method of the invention provides for a tactical team of four personnel, for example, to have LEU's mounted to their weapons, and are equipped with a flash-bang LEU. The tactical team is attempting a forced entry upon a building known to contain armed suspects. Prior to the mission, the team leader selects the modes of strobing that will be utilized on the CU and the team synchronizes the CU with their LEU's and LCD shutterglasses by holding down the "sync" button on each simultaneously. Immediately prior to entry, the team dons their LCD Shutterglasses and switches their LEU's to standby, and arms the flash-bang LEU. They breach the door and toss in the flash-bang LEU. The flash-bang detonates, disorienting the suspects, however, the night vision of the team is preserved because the detonation was timed to occur during an opaque period in the shutterglasses. The team turns their weapon mounted LEU's to "quick flash" and enters the building. The suspects continue to be disoriented by the quickly flashing strobes, however the team is not disoriented, because the strobe pulses are blocked by the quickly flashing shutterglasses. The team is then able to walk up and put handcuffs on the suspects.

Figure 6:
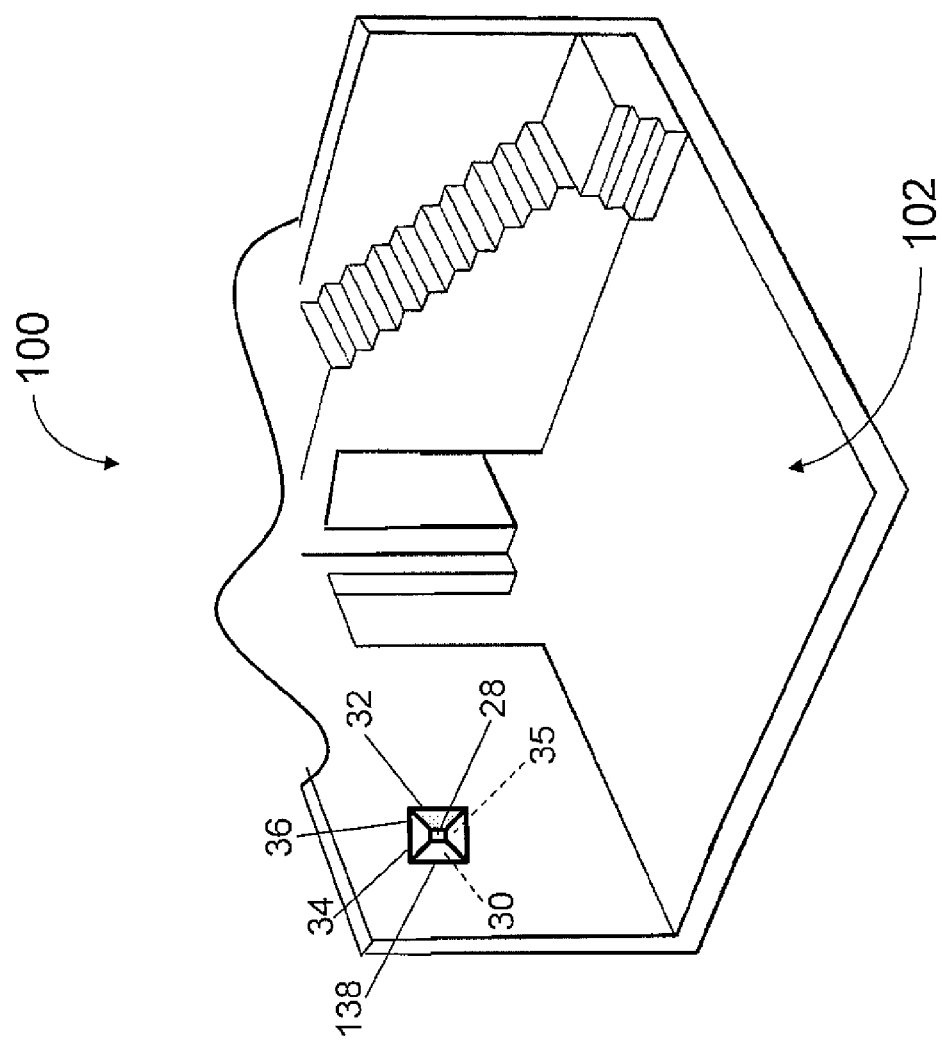
FIG. 6 is a perspective view of another example of a light emitting unit in a space of a building or structure incorporating features of the invention.

However, one skilled in the art will appreciate that various exemplary usages and/or methods can be provided, and various other types of light emitting units may be provided. For example, referring now also to FIG. 6, another embodiment of a light emitting unit is shown. In this embodiment the light emitting unit 138 comprises a light emitting portion 28, a timing circuit 30, a synchronizing button 32, a wireless interface 35, an on/standby/off switch 34, and a mode selector 36, substantially the same as the light emitting units 14, 16, 38 shown in FIGS. 1, 2. However, in this embodiment the light emitting unit is provided as a fixedly installed strobe in a space 102 of a building 100, such as mounted on a wall, for example. However, in alternate embodiments any suitable type of light emitting unit or mounting location may be provided. Furthermore, the LEU 138 may be suitably applied in various environments, for example, a home, a business, a prison, etc. For example, in these various environments, the eye protection 12 may be worn by home owners, business owners, security personnel, law enforcement personnel, corrections officers, etc. The LEU 138 is configured to be synchronized similarly as the light emitting units 14, 16, 38 to ensure that the flash occurs during a window when the shutterglasses are opaque. Additionally, the LEU 138 may be used in conjunction with an alarm system wherein the LEU may be automatically activated when the alarm system is triggered.

Figure 7:
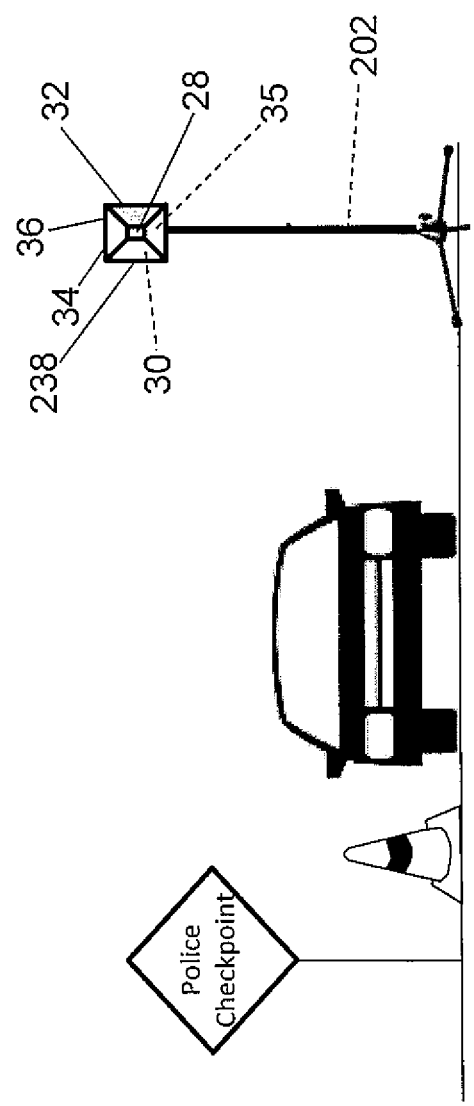
FIG. 7 is a front view of another example of a light emitting unit in a road block/checkpoint setting incorporating features of the invention.

According to another embodiment of the invention, the LEU may be provided in a portable configuration for use in police barriers, roadblocks, and checkpoints, for example. Referring now also to FIG. 7, the light emitting unit 238 comprises a light emitting portion 28, a timing circuit 30, a synchronizing button 32, a wireless interface 35, an on/standby/off switch 34, and a mode selector 36, substantially the same as the light emitting units 14, 16, 38, 138 shown in FIGS. 1, 2, 6. However, in this embodiment the light emitting unit is provided as a portable strobe configured to be mounted on a structure 202. In the example shown in FIG. 7, the LEU 238 is mounted on a portable tripod 202, however in alternate embodiments, the portable probe may be configured to be mounted on a utility pole, portable barricade, or any other suitable structure. In the non-limiting example illustrated in FIG. 7, the high intensity strobe 23 is provided at a checkpoint for non-lethally stopping vehicles, where checkpoint personnel can be equipped with shutterglasses, for example. However, in alternate embodiments, any suitable configuration may be provided.

According to some examples of the invention, the strobes need not be fired simultaneously, they can be fired sequentially or in groups. For example, strobe patterns need not be regular, and can be random or occulting. Additionally, patterns can move from left to right across a group of troops giving the false impression of movement.

According to some other examples of the invention, the glasses alone can be equipped with a sensor to opaque to block unsynchronized strobes (however, time can be an issue).

According to some other examples of the invention, a High/Low operation may be provided. For example, a tactical strobe/flashlight can be combined to provide low level lighting for operator visibility, while strobing periodically to maintain a tactical advantage.

According to some other examples of the invention, a strobe/LCD shutterglasses combination can be linked via cable and triggered from a common timer. In some other embodiments, the glasses unit may comprise a wired trigger, or may be triggered by the strobe. Additionally, other configurations such as a manual strobe/glasses trigger button, may be provided.

According to some other examples of the invention, the system may be configured for non-EMCON operation, where the shutterglasses can be turned on via a radio signal from the CU or LEU, so they are not shuttering prior to being needed.

Figure 8:
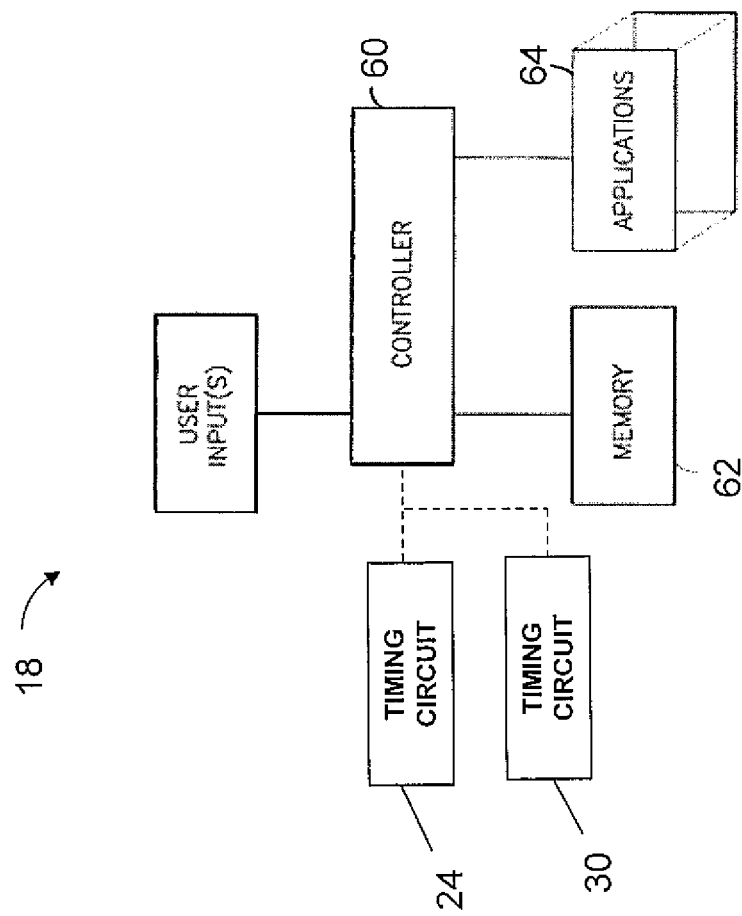
FIG. 8 is a schematic drawing illustrating components of the environment control system.

Referring now also to FIG. 8, the control unit may generally comprise a controller 60 such as a microprocessor for example. The electronic circuitry includes a memory 62 coupled to the controller 60, such as on a printed circuit board for example. The memory could include multiple memories including removable memory modules for example. The device has applications 64, such as software, which the user can use. The applications can include, any suitable type of applications. In some embodiments, one or more user inputs are coupled to the controller either directly or wirelessly. The timing circuits 24, 30 are also coupled to the controller 60. The control unit may programmed to automatically synchronize the LEUs with the shutterglasses. However, in an alternate embodiment, this might not be automatic. The user might need to actively synchronize the LEUs with the shutterglasses.

According some examples of the invention, a program storage device readable by a machine, tangibly embodying a program of instructions executable by the machine for performing operations to synchronize the LEUs and the shutterglasses may be provided.

It should be noted that the components/devices described above may be powered by any suitable power supply, such as a battery, or 120V AC.

It should further be noted that while the various exemplary embodiments of the invention have been described in connection with a tactical team of personnel seeking to detain suspects, one skilled in the art will appreciate that the invention is not necessarily so limited and that some embodiments may be provided for use in other non-police or non-military environments or applications.

The various examples of any one or more of the exemplary embodiments provide an environment control system having significant advantages and innovation when compared to conventional configurations. For example various embodiments provide for the ability to synchronize or coordinate multiple remote light sources (strobes, flash-bang or other light generating devices). Various embodiments further provide for wireless synchronization (rather than triggering) between light sources. Various embodiments further provide for a timing "window" concept. Various embodiments further provide for a combination of strobes with shutterglasses to make strobe flashes invisible to users. Various embodiments further provide for encryption of the synchronization signal.

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, an apparatus comprising: a control unit; a light source comprising a first timing circuit, wherein the light source is configured to emit light, and wherein the first timing circuit is configured to control a flashing of the light emitted by the light source; and an eye protection device comprising a second timing circuit and a lens portion, wherein the second timing circuit is configured to adjust a transparency and an opacity of the lens portion; wherein the control unit is configured to synchronize the flashing of the light emitted by the light source with the opacity of the lens portion.

An apparatus as above wherein the light source comprises a strobe unit.

An apparatus as above wherein the light source comprises a variable speed, high intensity strobe unit configured to provide about 0.5 to about 10 flashes per second (fps).

An apparatus as above wherein the eye protection device comprises shutterglasses.

An apparatus as above wherein the eye protection device comprises liquid crystal display (LCD) shutterglasses having LCD lenses, wherein the LCD lenses are configured to be substantially transparent, and wherein the LCD lenses are configured to turn substantially opaque when a voltage is applied to the LCD shutterglasses.

An apparatus as above wherein the second timing circuit is configured to control the timing of the opacity of the LCD lenses by controlling the voltage applied to the LCD shutterglasses.

An apparatus as above wherein the eye protection device comprises a wearable smart device.

An apparatus as above wherein the control unit is configured to synchronize the light source and the eye protection device such that the eye protection device is configured to be synchronized with light source to turn the lens portion opaque at the same time the light source is emitting light.

An apparatus as above wherein the light source is a hand-held light source.

An apparatus as above wherein the light source is fixedly mounted to a structure.

An apparatus as above wherein the light source is mounted to a weapon.

An apparatus as above wherein the eye protection device is synchronized with muzzle flash of the weapon.

An apparatus as above wherein the light source comprises a flash bang grenade.

An apparatus as above wherein the control unit is housed in a portable electronic device.

In another exemplary embodiment, a method comprising: emitting light from a light source, wherein the emitted light comprises a flashing light; adjusting a lens portion of an eye protection device from a substantially transparent state to a substantially opaque state; and synchronizing the emitting of the light with the adjusting of the lens portion.

A method as above wherein the flashing light comprises a variable speed, high intensity, strobe light.

A method as above wherein the synchronizing further comprises synchronizing the flashing of the strobe light with the adjustment of the lens portion to the substantially opaque state such that a wearer of the eye protection device is protected from effects of the strobe light.

In another exemplary embodiment, a non-transitory computer readable medium embodied with a computer program comprising computer program instructions which when loaded into a processor enable the processor to: control a flashing light emitted from a light source; and adjust a lens portion of an eye protection device in response to the flashing light such that the lens portion is adjusted between substantially transparent and substantially opaque.

A non-transitory computer readable medium as above further comprising synchronizing the flashing light with the adjustment of the lens portion to be substantially opaque.

A non-transitory computer readable medium as above wherein a first timing circuit is configured to control the flashing light and wherein a second timing circuit is configured to control the adjustment of the lens portion.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. An apparatus comprising:
   a controller comprising a processor and a memory, wherein the processor is connected to a first timing circuit and a second timing circuit;
   a light source comprising the first timing circuit, wherein the light source is configured to emit light, and wherein the first timing circuit is configured, with the processor and the memory, to control a flash rate of the light emitted by the light source; and
   an eye protection device comprising the second timing circuit and a lens portion, wherein the second timing circuit is configured, with the processor and the memory, to apply a voltage to the lens portion to adjust a transparency and an opacity of the lens portion;

wherein the processor and the memory are configured to synchronize the flashing of the light emitted by the light source with the opacity of the lens portion when a synchronize operation is performed.

2. An apparatus as in claim 1 wherein the light source comprises a strobe unit.

3. An apparatus as in claim 1 wherein the light source comprises a variable speed, high intensity strobe unit configured to provide a flash rate of about 0.5 to about 10 flashes per second (fps).

4. An apparatus as in claim 1 wherein the eye protection device comprises shutterglasses.

5. An apparatus as in claim 1 wherein the eye protection device comprises liquid crystal display (LCD) shutterglasses having LCD lenses, wherein the LCD lenses are configured to be substantially transparent, and wherein the LCD lenses are configured to turn substantially opaque when the voltage is applied to the LCD shutterglasses.

6. An apparatus as in claim 5 wherein the second timing circuit is configured to control the timing of the opacity of the LCD lenses by controlling the voltage applied to the LCD shutterglasses.

7. An apparatus as in claim 1 wherein the eye protection device comprises a wearable smart device.

8. An apparatus as in claim 1 wherein the timing circuits, with the processor and the memory, are configured to cause the apparatus to synchronize the light source and the eye protection device such that the eye protection device is configured to be synchronized with light source to turn the lens portion opaque at the same time the light source is emitting light.

9. An apparatus as in claim 1 wherein the light source is a hand-held light source.

10. An apparatus as in claim 1 wherein the light source is fixedly mounted to a structure.

11. An apparatus as in claim 1 wherein the light source is mounted to a weapon.

12. An apparatus as in claim 11 wherein the eye protection device is synchronized with muzzle flash of the weapon.

13. An apparatus as in claim 1 wherein the light source comprises a flash bang grenade.

14. An apparatus as in claim 1 wherein the controller is housed in a portable electronic device.

15. A method comprising:
emitting light from a light source, wherein the emitted light comprises a flashing light having a flash rate;
applying a voltage to a lens portion of an eye protection device to adjust the lens portion from a substantially transparent state to a substantially opaque state; and
synchronizing the emitting of the light with the adjusting of the lens portion when a synchronize operation between the light source and the eye protection device is performed.

16. A method as in claim 15 wherein the flashing light comprises a variable speed, high intensity, strobe light.

17. A method as in claim 16 wherein the synchronizing further comprises synchronizing the flashing of the strobe light with the adjustment of the lens portion to the substantially opaque state such that a wearer of the eye protection device is protected from effects of the strobe light.

18. A non-transitory computer readable medium embodied with a computer program comprising computer program instructions which when loaded into a processor enable the processor to:
control a flash rate of a flashing light emitted from a light source; and
apply a voltage to a lens portion of an eye protection device in response to the flashing light such that the applied voltage to the lens portion adjusts between substantially transparent and substantially opaque.

19. A non-transitory computer readable medium as in claim 18 further comprising synchronizing the flashing light with the adjustment of the lens portion to be substantially opaque.

20. A non-transitory computer readable medium as in claim 18 wherein a first timing circuit is configured to control the flashing light and wherein a second timing circuit is configured to control the adjustment of the lens portion.

* * * * *